United States Patent [19]

Gerlach et al.

[11] Patent Number: 5,227,368
[45] Date of Patent: Jul. 13, 1993

[54] ENDOTOXIN-INDUCED THROMBOSIS FACTOR WHICH INDUCES PROCOAGULANT ACTIVITY IN ENDOTHELIAL CELLS

[75] Inventors: Herwig Gerlach, New York; David Stern, Great Neck, both of N.Y.

[73] Assignee: The Trustees of Columbia University in the City of New York, N.Y.

[21] Appl. No.: 486,311

[22] Filed: Feb. 28, 1990

[51] Int. Cl.$^5$ .................. A61K 37/00; C07K 3/00; C07K 7/00; C07K 15/00

[52] U.S. Cl. ............................ 514/12; 530/324; 530/350; 530/351

[58] Field of Search ............. 514/12; 530/324, 350, 530/351, 387

[56] References Cited

PUBLICATIONS

Nawroth et al., J. Exp. Med., vol. 163, pp. 740–745, Mar. 1986.
Beutler et al., J. Exp. Med., vol. 163, pp. 984–995, May 1985.

Primary Examiner—Merrell C. Cashion, Jr.
Assistant Examiner—A. M. Davenport
Attorney, Agent, or Firm—John P. White

[57] ABSTRACT

This invention provides a purified endotoxin-induced thrombosis factor, preferably an endotoxin-induced thrombosis factor characterized by an apparent molecular weight between about 50,000 and 65,000 daltons, more specifically about 55,000 daltons, on reduced and nonreduced SDS-polyacrylamide gels, by maximal recovery on elution from such gels at 52,000 to 58,000 daltons, by the ability to migrate as a single band on such gels, by the ability to precipitate in ammonium sulfate at saturations from 40% to 70%, by the ability to precipitate in polyethylene glycol at concentrations above 15%, by high hydrophobicity, by the ability to bind weakly to a hydroxylapatite column and to a lentil lectin column, by the ability to bind tightly to a hydrophobic interaction resin and smear off with ethylene glycol, and by the ability to bind tightly to a reverse-phase column and elute more effectively with isopropanol than with acetonitrile, by the ability to bind to an anion exchange resin over a pH range from 5 to 10, by the inability to bind to a cation exchange resin, by resistance to acid denaturation up to 30 minutes, resistance to polymyxin, sensitivity to heating at 95° C. for 30 minutes, and sensitivity to trypsin exposure for 24 hours. Another characteristic of a purified endotoxin-induced thrombosis factor that it maximally induces tissue factor after six to eight hours, and continues to induce tissue factor for up to sixty hours. This invention also provides purified nucleic acid molecules, antibodies, an inhibitor, an antagonist, pharmaceutical compositions, methods of treatment, and methods of preparation all directed to endotoxin-induced thrombosis factor.

4 Claims, 1 Drawing Sheet

ENDOTOXIN-INDUCED THROMBOSIS FACTOR WHICH INDUCES PROCOAGULANT ACTIVITY IN ENDOTHELIAL CELLS

BACKGROUND OF THE INVENTION

A salient feature of the septic shock state due to Gram negative bacteria is the presence of abnormalities of the coagulation mechanism, as manifested by disseminated intravascular coagulation, adrenal hemorrhage, thrombus formation and other well-known syndromes. Activation of coagulation in this setting is thought to result from the expression of tissue factor, a procoagulant cell surface cofactor, in the intravascular space by monocytes and endothelial cells. The pathogenesis of this host response to the Gram negative bacteria, especially the lipopolysaccharide (LPS), or endotoxin component of the cell wall, is thought to involve the elaboration of mediators, termed cytokines, such as tumor necrosis factor/cachectin (TNF) (1-3) and Interleukin 6, whose effects in target tissues result in many of the clinical findings characteristic of the septic shock state. However, the coagulopathy of Gram negative shock is not duplicated by any of the known endotoxin-derived host response mediators, leading us to identify alternate products which result in the induction of cellular tissue factor. Macrophages have been identified as the likely source of such products following exposure to endotoxin, a toxic component of the cell wall of Gram negative bacteria.

Macrophage mediators have a central role in the host response to multiple injurious stimuli. The study of endotoxin-elicited macrophage mediators, such as tumor necrosis factor (TNF), certain interleukins and macrophage inflammatory proteins, has emphasized the potential significance of these cytokines in the pathophysiology of the septic shock state. Abnormalities of the coagulation mechanism are a prominent feature of septic shock, and result, in large part, from the induction of tissue factor in cells in the intravascular space (especially monocytes and, probably, endothelial cells as well). Studies in which known cytokines have been infused into animals have not succeeded in reproducing the serious coagulopathy associated with Gram negative sepsis.

We have characterized a novel polypeptide (endotoxin-induced thrombosis factor) synthesized and secreted by macrophages (RAW 264.7) in response to endotoxin which induces tissue factor in monocytes and endothelium. Endotoxin-induced thrombosis factor has a role in the pathogenesis of shock and thrombosis, as a factor which can induce tumor necrosis (its activities in vitro suggest it will result in tumor necrosis in vivo), and in other clinically relevant situations (especially as a promoter of angiogenesis and white cell proliferation/development).

Septic shock is associated with profound abnormalities of the coagulation mechanism. Although known macrophage mediators, such as tumor necrosis factor (TNFα), reproduce certain aspects of the shock syndrome, they do not elicit the full range of coagulation abnormalities seen with lipopolysaccharide (LPS). The murine macrophage cell line RAW 264.7 was exposed to LPS and conditioned medium was subjected to sequential anion exchange chromatography, gel elution, and reversed phase (C2/C8) chromatography. The final product, which was homogeneous on SDS-PAGE, was a $\approx$55 kDa polypeptide (endotoxin-induced thrombosis factor) with a unique amino-terminal sequence, which induced tissue factor activity and antigen in cultured human ECs. The activity of endotoxin-induced thrombosis factor was destroyed by heat and treatment with trypsin. Half-maximal induction of tissue factor on ECs occurred at a concentration of $\approx$150 pM. In addition, the polypeptide was effective in inducing tissue factor activity in human monocytes. In conclusion, the new polypeptide is an LPS-elicited macrophage mediator which may contribute to the coagulopathy characteristic of Gram negative septicemia.

Transformed murine macrophages (RAW) secrete the novel polypeptide, endotoxin-induced thrombosis factor, whose expression is elicited after exposure to LPS and which potently induces tissue factor in human endothelial cells and monocytes. This factor is responsible for the majority of the endothelial cell tissue factor induced by LPS. Endotoxin-induced thrombosis factor has an important role in the pathogenesis of the coagulopathy associated with Gram negative sepsis. This invention is a novel polypeptide released by RAW cells stimulated by endotoxin. Inhibiting activity of endotoxin-induced thrombosis factor will prevent abnormal formation of blood clots in septic shock and other conditions.

Cytokines, specifically interleukin-1 and tumor necrosis factor, are induced by endotoxin and induce tissue factor in endothelial cells. Interleukin-6 is also induced by endotoxin, but does not induce tissue factor. However, the novel polypeptide, endotoxin-induced thrombosis factor, is an especially potent tissue factor inducer, and as such is responsible for the major amount of tissue factor induction in Gram negative sepsis.

SUMMARY OF THE INVENTION

This invention provides a purified endotoxin-induced thrombosis factor, preferably an endotoxin-induced thrombosis factor characterized by an apparent molecular weight between about 50,000 and 65,000 daltons, more specifically about 55,000 daltons, on reduced and nonreduced SDS-polyacrylamide gels, by maximal recovery on elution from such gels at 52,000 to 58,000 daltons, by the ability to migrate as a single band on such gels, by the ability to precipitate in ammonium sulfate at saturations from 40% to 70%, by the ability to precipitate in polyethylene glycol at concentrations above 15%, by high hydrophobicity, by the ability to bind weakly to a hydroxylapatite column and to a lentil lectin column, by the ability to bind tightly to a hydrophobic interaction resin and smear off with ethylene glycol, and by the ability to bind tightly to a reverse-phase column and elute more effectively with isopropranol than with acetonitrile, by the ability to bind to an anion exchange resin over a pH range from 5 to 10, by the inability to bind to a cation exchange resin, by resistance to acid denaturation up to 30 minutes, resistance to polymyxin, sensitivity to heating at 95.C for 30 minutes, and sensitivity to trypsin exposure for 24 hours. Another characteristic of a purified endotoxin-induced thrombosis factor is that it maximally induces tissue factor after six to eight hours, and continues to induce tissue factor for up to sixty hours.

This invention provides purified nucleic acid molecules encoding the endotoxin-induced thrombosis factor.

This invention further provides an antibody directed to an epitope comprising an active site of endotoxin-induced thrombosis factor, such as a monoclonal antibody.

This invention also provides a molecule which acts as an endotoxin-induced thrombosis factor inhibitor, and a molecule which acts as an endotoxin-induced thrombosis factor antagonist.

This invention provides a pharmaceutical composition comprising an amount of an antibody directed to an epitope comprising an active site of endotoxin-induced thrombosis factor effective to inhibit the activity of the factor and a pharmaceutically acceptable stabilizer.

This invention also provides a pharmaceutical composition comprising an amount of an inhibitor directed to endotoxin-induced thrombosis factor effective to inhibit the activity of the factor and a pharmaceutically acceptable carrier.

This invention further provides a pharmaceutical composition comprising an amount of an antagonist, such as a mutant endotoxin-induced thrombosis factor effective to inhibit the effects of endotoxin-induced thrombosis factor by binding to its receptor, and a pharmaceutically acceptable carrier.

This invention provides a pharmaceutical composition comprising an amount of endotoxin-induced thrombosis factor effective to cause tumor necrosis and a pharmaceutically acceptable carrier.

This invention also provides a pharmaceutical composition comprising an amount of endotoxin-induced thrombosis factor effective to promote formation and differentiation of blood vessels and a pharmaceutically acceptable carrier, and a pharmaceutical composition comprising an amount of endotoxin-induced thrombosis factor effective to promote proliferation and differentiation of white blood cells and a pharmaceutically acceptable carrier.

This invention provides a method for treating a subject in septic shock comprising administering to the subject an amount of a pharmaceutical composition effective to inactivate endotoxin-induced thrombosis factor and thereby reverse intravascular coagulation caused by the induction of tissue factor by endotoxin-induced thrombosis factor.

This invention provides a method for treating a subject having a tumor which comprises administering to the subject an amount of endotoxin-induced thrombosis factor and a pharmaceutically acceptable carrier effective to necrotize the tumor.

This invention also provides a method for treating a subject having blood vessel damage which comprises administering to the subject an amount of endotoxin-induced thrombosis factor and a pharmaceutically acceptable carrier effective to promote blood vessel growth.

This invention further provides a method for treating a subject having a white blood cell disorder which comprises administering to the subject an amount of endotoxin-induced thrombosis factor and a pharmaceutically acceptable carrier effective to promote white blood cell proliferation and differentiation.

This invention provides a method for preparing endotoxin-induced thrombosis factor which comprises inducing cells to express endotoxin-induced thrombosis factor, recovering the factor from the resulting cells, and purifying the factor so recovered.

This invention also provides a method for preparing endotoxin-induced thrombosis factor by use of recombinant DNA technology which comprises the use of methods well known in the art.

DETAILED DESCRIPTION OF THE INVENTION

Figure 1:
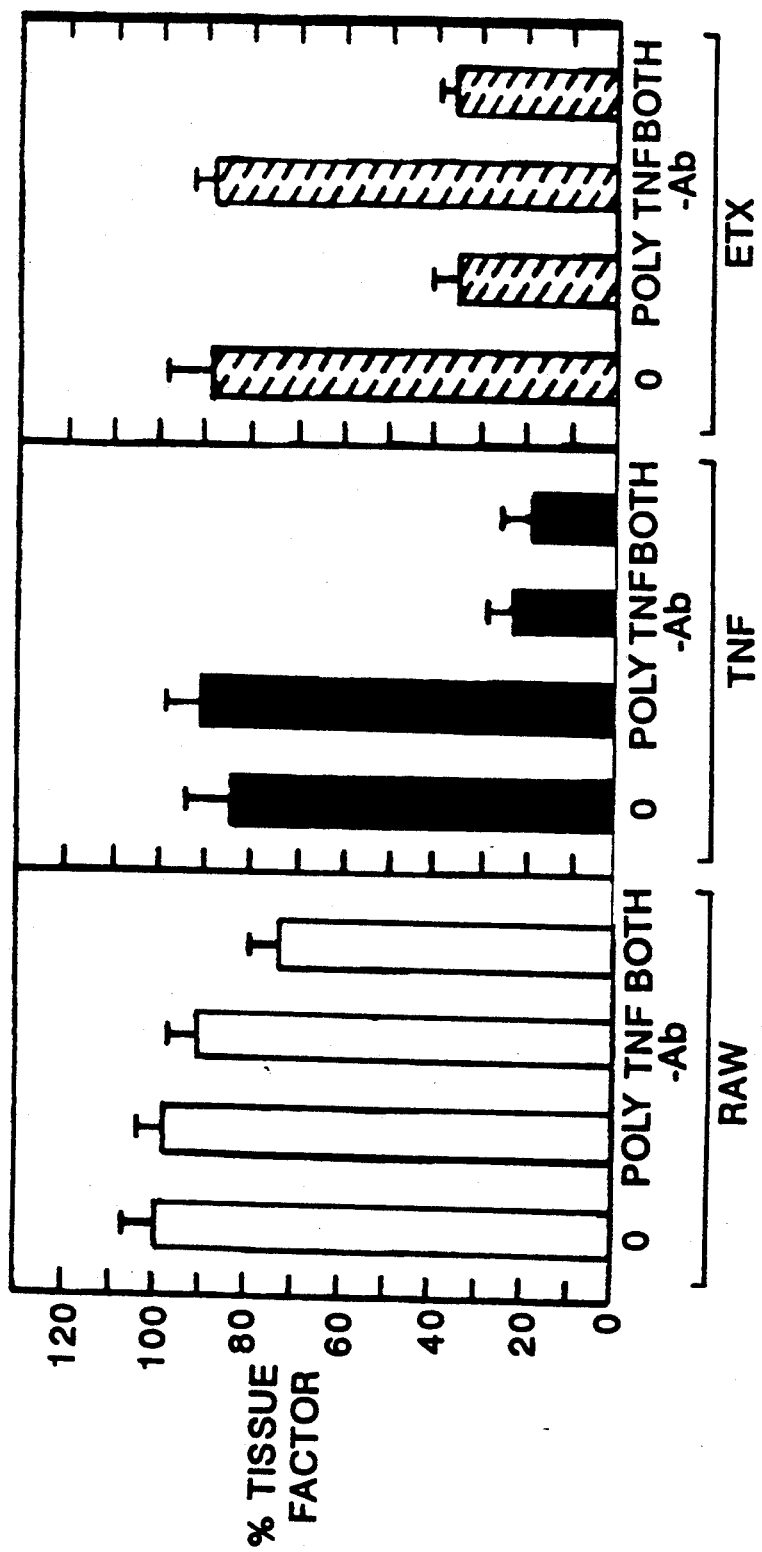
FIG. 1. Effect of endotoxin-induced RAW cell supernatant (left panel), TNF (middle panel) and endotoxin (right panel) on endothelial tissue factor activity. Left panel. RAW cells were incubated with RPMI containing LPS (1 $\mu$g/ml) as described in the text, supernatants were chromatographed ten times over Detoxi-gel resin, and then incubated with confluent monolayers of HUVEC alone, in the presence of polymyxin (1 $\mu$g/ml; poly), anti-murine TNF IgG (1:200 dilution, final; samples were pre-incubated with the latter for 30 min at 37° C.; TNF Ab) or in the presence of both agents together. Endothelial tissue factor was measured in the coagulant assay described in the text. 100% tissue factor induction was arbitrarily defined as the tissue factor activity induced by RAW supernatant alone. Middle panel. HUVECs were incubated as in the other two panels but with RPMI containing purified murine TNF (purchased from Genzyme) at a concentration to induce the same amount of tissue factor as in the other two experiments (shown in the other panels). As indicated, polymyxin, antibody to TNF or both of these agents were also added. Right panel. HUVECs were incubated as above, but with RPMI containing endotoxin (ETX) at a concentration adjusted to induce the same amount of tissue factor in endothelium. As indicated, polymyxin, antibody to TNF or both these agents were also added. In this context, endotoxin is the same as LPS. In each case, the mean +SD is shown.

This invention provides a purified endotoxin-induced thrombosis factor, preferably an endotoxin-induced thrombosis factor characterized by an apparent molecular weight between about 50,000 and 65,000 daltons, more specifically about 55,000 daltons, on reduced and nonreduced SDS-polyacrylamide gels, by maximal recovery on elution from such gels at 52,000 to 58,000 daltons, by the ability to migrate as a single band on such gels, by the ability to precipitate in ammonium sulfate at saturations from 40% to 70%, by the ability to precipitate in polyethylene glycol at concentrations above 15%, by high hydrophobicity, by the ability to bind weakly to a hydroxylapatite column and to a lentil lectin column, by the ability to bind tightly to a hydrophobic interaction resin and smear off with ethylene glycol, and by the ability to bind tightly to a reverse-phase column and elute more effectively with isopropanol than with acetonitrile, by the ability to bind to an anion exchange resin over a pH range from 5 to 10, by the inability to bind to a cation exchange resin, by resistance to acid denaturation up to 30 minutes, resistance to polymyxin, sensitivity to heating at 95° C. for 30 minutes, and sensitivity to trypsin exposure for 24 hours. Another characteristic of a purified endotoxin-induced thrombosis factor is that it maximally induces tissue factor after six to eight hours, and continues to induce tissue factor for up to sixty hours.

This invention provides a purified nucleic acid molecule encoding the endotoxin-induced thrombosis factor, for example a cDNA molecule, an isolated genomic DNA molecule, or an isolated RNA molecule. Such nucleic acid can be readily obtained by one skilled in the art utilizing well known methods, e.g., the preparation of oligonucleotide probes and the use of such probes to obtain the nucleic acids, such probes being based in turn upon the amino acid sequence of endotoxin-induced thrombosis factor, which may be readily obtained using conventional methods of peptide sequencing. For example, the amino acid sequence of endotoxin-induced thrombosis factor is determined by cleaving the protein into its component peptide fragments, then reacting each peptide fragment with known chemicals that remove and identify individual amino acids starting from either the N-terminal or the C-terminal end, and finally determining how the peptide fragments overlap to assemble the complete sequence of the protein. The whole procedure has been automated and may be performed on a machine. When the amino acid sequence is known, a DNA acid probe encoding any part of this sequence is made on a DNA synthesizer. mRNA purified from cells known to express endotoxin-induced thrombosis factor, for example macrophages exposed to lipopolysaccharide, is then contacted with the probe, and the mRNA that hybridizes to the probe is isolated. cDNA is made from the mRNA with reverse transcriptase, and can be used as a probe for genomic DNA encoding endotoxin-induced thrombosis factor, and also sequenced.

This invention further provides an antibody directed to an epitope comprising an active site of endotoxin-induced thrombosis factor, such as a monoclonal antibody. Such antibodies can be readily obtained by one skilled in the art utilizing well known methods. For example, antibodies to endotoxin-induced thrombosis factor are raised by injecting the protein into an animal, isolating antiserum from the animal, and using well-known immunological techniques such as precipitation reactions to purify antibodies directed to endotoxin-induced thrombosis factor. Monoclonal antibodies are obtained by isolating B-lymphocytes from the injected animal, selecting those which produce antibodies directed to endotoxin-induced thrombosis factor, fusing them with myeloma cells, and thereby producing hybridomas which produce antibodies directed to endotoxin-induced thrombosis factor. Antibodies directed to an epitope which is an active site of endotoxin-induced thrombosis factor are selected by contacting antibodies directed to endotoxin-induced thrombosis factor with cells that have been induced by endotoxin-induced thrombosis factor to produce tissue factor, and selecting the antibody that reverses the induction effects of the factor. This antibody will bind not only to the factor, but to its active site.

This invention also provides a molecule which acts as an endotoxin-induced thrombosis factor inhibitor. The inhibitor is isolated by in vitro binding assays with purified endotoxin-induced thrombosis factor using methods well known in the art. For example, natural or synthetic molecules are contacted with endotoxin-induced thrombosis factor to determine whether they are capable of binding to endotoxin-induced thrombosis factor and inhibiting its activity. Then, the molecule which inhibits the activity of the factor is selected by contacting a molecule directed to endotoxin-induced thrombosis factor with cells that have been induced by endotoxin-induced thrombosis factor to produce tissue factor, and selecting the molecule that reverses the induction effects of the factor. This molecule is an inhibitor of endotoxin-induced thrombosis factor.

This invention further provides a molecule which acts as an endotoxin-induced thrombosis factor antagonist. The antagonist is isolated by methods well known in the art. For example, natural or synthetic molecules are contacted with cells that have been induced by endotoxin-induced thrombosis factor. Those molecules that reverse the effects of the factor are acting as antagonists. An antagonist can act by binding to the same receptor to which the factor binds, but without inducing the response that the factor induces. Another method for isolating the antagonist is to isolate the receptor for the factor by exposing cells to labeled factor and isolating receptor labeled thereby, and then performing binding assays with the receptor using methods well known in the art to determine which molecules bind the receptor. Then, the molecules are contacted with cells to determine which act as antagonists by binding to the receptor *without* inducing tissue factor. An example of such an antagonist is a mutant endotoxin-induced thrombosis factor which binds to the cell-surface receptor for endotoxin-induced thrombosis factor but does not induce tissue factor.

This invention provides a pharmaceutical composition comprising an amount of an antibody directed to an epitope comprising an active site of endotoxin-induced thrombosis factor effective to inhibit the activity of the factor and a pharmaceutically acceptable stabilizer. The antibody binds to the factor so that the factor cannot bind to its receptor and thereby induce a cell to produce the tissue factor which stimulates coagulation. The pharmaceutical composition further comprises one or more antibodies directed to selected cytokines and an inhibitor of lipopolysaccharide effective to inhibit the induction of tissue factor, and a pharmaceutically acceptable stabilizer. Specifically, the selected cytokine is tumor necrosis factor, which also induces tissue factor but to a lesser extent than does endotoxin-induced thrombosis factor. Lipopolysaccharide (LPS) induces cells to produce endotoxin-induced thrombosis factor. Therefore antibodies to the cytokine tumor necrosis factor, which have a partially protective effect on mice infused with LPS, and LPS inhibitors, act in conjunction with an antibody or inhibitor which binds directly to endotoxin-induced thrombosis factor, to limit its effects. Antibodies have a fairly long half-life in the circulation but are broken down when ingested, therefore are suitable for injection with a stabilizer, but not for oral administration. An example of a pharmaceutically acceptable stabilizer is albumin.

This invention also provides a pharmaceutical composition comprising an amount of an inhibitor directed to endotoxin-induced thrombosis factor effective to inhibit the effects of endotoxin-induced thrombosis factor and a pharmaceutically acceptable carrier. Examples of pharmaceutically acceptable carriers are distilled water, saline, pH and ionically balanced fluids, and solids such as capsules and tablets.

This invention further provides a pharmaceutical composition comprising an amount of an antagonist, such as a mutant endotoxin-induced thrombosis factor effective to inhibit the effects of endotoxin-induced thrombosis factor by binding to its receptor and a pharmaceutically acceptable carrier. Examples of pharmaceutically acceptable carriers are distilled water, saline, Ph and ionically balanced fluids, and solids such as capsules and tablets.

This invention provides a pharmaceutical composition comprising an amount of endotoxin-induced thrombosis factor effective to cause tumor necrosis and a pharmaceutically acceptable carrier. The pharmaceutical composition comprises factors augmenting the effects of tumor necrosis factor and a pharmaceutically acceptable carrier. Examples of such augmenting factors are tumor necrosis factor/cachectin, flavone acetic acid, or meth A factor. Examples of pharmaceutically acceptable carriers are distilled water, saline, pH and ionically balanced fluids, and solids such as capsules and tablets.

This invention also provides a pharmaceutical composition comprising an amount of endotoxin-induced thrombosis factor effective to promote formation and differentiation of blood vessels and a pharmaceutically acceptable carrier, and a pharmaceutical composition comprising an amount of endotoxin-induced thrombosis factor effective to promote proliferation and differentiation of white blood cells and a pharmaceutically acceptable carrier. Examples of pharmaceutically acceptable carriers are distilled water, saline, pH and ionically balanced fluids, and solids such as capsules and tablets.

This invention provides a method for treating a subject in septic shock comprising administering to the subject an amount of a pharmaceutical composition effective to inactivate endotoxin-induced thrombosis factor and thereby reverse intravascular coagulation caused by the induction of tissue factor by endotoxin-induced thrombosis factor. The pharmaceutical composition comprises an amount of an antibody or an inhibitor directed to endotoxin-induced thrombosis factor effective to inhibit the activity of the factor and a pharmaceutically acceptable carrier or stabilizer. The pharmaceutical composition that comprises antibody additionally comprises one or more antibodies directed to selected cytokines and an inhibitor of lipopolysaccharide effective to inhibit the induction of tissue factor. The pharmaceutical composition alternatively comprises an amount of an antagonist, such as a mutant endotoxin-induced thrombosis factor effective to inhibit the effects of endotoxin-induced thrombosis factor by binding to its receptor.

This invention provides a method for treating a subject having a tumor which comprises administering to the subject an amount of endotoxin-induced thrombosis factor and a pharmaceutically acceptable carrier effective to necrotize the tumor. The pharmaceutical composition further comprises factors augmenting the effects of tumor necrosis factor and a pharmaceutically acceptable carrier. Examples of such augmenting factors are tumor necrosis factor/cachectin, flavone acetic acid, or meth A factor.

This invention also provides a method for treating a subject having blood vessel damage which comprises administering to the subject an amount of endotoxin-induced thrombosis factor and a pharmaceutically acceptable carrier effective to promote blood vessel growth.

This invention further provides a method for treating a subject having a white blood cell disorder which comprises administering to the subject an amount of endotoxin-induced thrombosis factor and a pharmaceutically acceptable carrier effective to promote white blood cell proliferation and differentiation.

This invention provides a method for preparing endotoxin-induced thrombosis factor which comprises inducing cells to express endotoxin-induced thrombosis factor, recovering the factor from the resulting cells, and purifying the factor so recovered. A detailed example of a method for preparing the factor is provided infra in Experimental Details.

This invention also provides a method for preparing endotoxin-induced thrombosis factor by use of recombinant DNA technology which comprises the use of methods well known in the art. For example, isolated nucleic acid encoding endotoxin-induced thrombosis factor is inserted in a suitable vector, such as an expression vector. A suitable host cell, such as a bacterial cell, or a eucaryotic cell such as a yeast cell, is transfected with the vector. Endotoxin-induced thrombosis factor is isolated from the culture medium by affinity purification or by chromatography or by other methods well known in the art.

This invention will be better understood by reference to the Experimental Details which follow, but those skilled in the art will readily appreciate that the specific experiments detailed are only illustrative of the invention, and should not be construed to limit in any way the invention as set forth in the claims which follow thereafter.

Experimental Details

Endotoxin-induced thrombosis factor has been purified from supernatants of endotoxin-treated RAW cells by chromatography (FPLC, HPLC) and preparative SDS-PAGE. The final product is a trypsin-sensitive polypeptide, Mr $\approx$55 kDa on reduced SDS-PAGE, which has a unique sequence, based on 17 residues from the amino terminus. Elution of purified endotoxin-induced thrombosis factor from reduced SDS-PAGE demonstrated that this material induced tissue factor synthesis and expression in a time- and dose-dependent manner in human peripheral blood monocytes and cultured human endothelium. Endotoxin-induced thrombosis factor is at least as potent as TNF for induction of procoagulant activity in endothelium and may be more potent than TNF on monocytes.

Materials and Methods

Evidence leading to the identification of endotoxin-induced thrombosis factor:

Murine macrophages (a transformed cell line, RAW 264.7, obtained from the American Type Culture Collection, Rockville, Md.) are incubated with LPS (1 $\mu$g/ml; Difco) for 16 hours at 37° C. The supernatant is harvested and applied to DeToxi-gel (Pierce) columns ten times, to lower the LPS concentration. These LPS-induced RAW supernatants have no procoagulant activity by themselves, but when incubated with cultured endothelium or macrophages, they can induce the expression of tissue factor, an activator of coagulation. The RAW supernatant is next incubated with monolayers of human umbilical vein endothelial cells, cultured by well-established techniques (4), alone or in the presence of polymyxin B (1 $\mu$g/ml) and/or antibody to murine TNF (purchased from Genzyme and used at a 1:200 dilution), and tissue factor activity is assessed using a one-stage procoagulant assay, as we have described previously. The results are shown in FIG. 1. If the tissue factor induced by RAW supernatant in the absence of other agents is termed 100%, then this amount can be diminished somewhat by polymxin B (poly) or antibody to TNF (TNF-Ab), but over 60–70% of the tissue factor inducing activity remains in the presence of both of these inhibitors. This indicates that a major component of the tissue factor-inducing activity of RAW supernatants is not due to TNF or residual LPS. These findings prompted us to purify the molecular species responsible for the bulk of the tissue factor inducing activity in the LPS-elicited RAW supernatants.

Purification of Endotoxin-induced thrombosis factor:

Endotoxin-induced thrombosis factor is a monocyte-derived protein which is produced after incubation of cultured monocytes with LPS, and it induces procoagulant activity in cultured human endothelial cells. In this section, culture techniques, the procedure for production of the factor, assay systems to detect it, and purification steps to prepare it are described.

Murine monocytes were cultured according to the method of Beutler et al (5): the cells (RAW 264.7, obtainable from American Type Culture Collection, Rockville, Md.) were planted in 150 mm-plates, using RPMI 1640 (with glutamine and bicarbonate) containing 10% bovine serum (Hyclone, Sterile Systems) and 14 mM HEPES-buffer, pH 7.4. Refeeding of the cells took place every two to three days. After seven to ten days, the cells reached confluence and were subcultured, using a 1:5 split ratio, into 600 cm² plates, by scraping the cells into a suspension and diluting the suspension in fresh medium added to the new culture vessel. After the cells reached confluence in these plates, they were refed as described above, and, after 24 hours, they were washed ten times with sterile Hanks' Balanced Salt Solution (HBSS), containing bicarbonate and HEPES (14 mM, pH 7.4). After the last washing cycle, the HBSS was aspirated, and RPMI 1640 containing LPS (1 μg/ml; DIFCO) and 14 mM HEPES, pH 7.4 was added. After an incubation period of 16 to 18 hours at 37° C., the culture supernatant was decanted, centrifuged (10,000 rpm, 15 min), filtered (0.2 μm filter), and frozen at −80° C. Culture supernatants from unstimulated cells were prepared by an identical procedure except that LPS was not added to the medium.

Human umbilical vein endothelial cells (HUVEC's) were cultured as described (6). Briefly, the cells were harvested from human umbilical cords not older than 24 hours, using collagenase, and planted in 25 cm² flasks, precoated with endotoxin-free gelatin. The culture medium consisted of Medium 199 containing glutamine, 15% fetal bovine serum, 5% human serum, penicillin-/streptomycin, bicarbonate and 14 mM HEPES, pH 7.4. A 0.2% trypsin solution was used to subculture the cells, after they achieved confluence.

To test the procoagulant activity of the cell-supernatant of the stimulated monocytes and the purified fractions (see below), HUVEC's were planted in gelatinized 6-well plates, using the same technique as described above. After reaching confluence, the cells were refed, and 24 hours later, samples were added to the medium, at a final dilution of 1:50 to 1:500. In addition, polymyxin B (1 μg/ml; SIGMA) and/or rabbit-anti-murine tumor necrosis factor(TNF)antiserum (GENZYME, final dilution 1:200) was added to assess the effects of remaining LPS and/or murine TNF, respectively. Following a 6 hour incubation period at 37° C., endothelial cell-dependent procoagulant activity was tested using a one-stage recalcification time: cells were scraped with a rubber policeman and pipetted into glass tubes. The cells were washed twice with veronal buffer (sodium acetate 7 mM, sodium barbital 7 mM, sodium chloride 140 mM, final pH 7.4) by centrifugation (4,000 rpm, 5 min) and resuspended in 0.5 ml buffer. After the second washing step, the cells were resuspended in 0.1 ml buffer, and then in sequence 0.1 ml human plasma and 0.1 ml calcium chloride (20 mM) were added. After the final addition, the time required for formation of a fibrin clot at 37° C. was measured.

The purification of endotoxin-induced thrombosis factor was performed as follows: frozen supernatant derived from LPS-stimulated cells was thawed and precipitated with 80% ammonium sulfate at room temperature for 3 hours. After centrifugation (10,000 rpm, 30 min) the pellet was dissolved in tris-buffer (20 mM, pH 7.4) containing 0.1% octyl-β-glucoside and centrifuged again (15,000 rpm, 30 min.). The final supernatant was dialyzed versus tris-buffer saline (tbs, 20 mM tris, 50 mM NaCl, pH 7.4) for 24 hours at 4° C. Afterwards, the supernatant was run ten times over a Detoxigel-column (Pierce), loaded on a Mono Q 10/10 column (Pharmacia) using an FPLC system (Pharmacia), one-step-eluted with tris 20 mM and 600 mM NaCl, and dialyzed again as described above. Samples which induced procoagulant activity in endothelial cells were pooled and loaded on a preparative SDS-agarose gel (6% agarose in tris-borate, FMC) and run by the method of Laemmli (6). Note that our samples were not boiled prior to loading on the gel, but only incubated with the reducing buffer for two hours at 37° C. After electrophoresis, lanes of the gel were cut into 2 mm-slices, and each slice was cut in small pieces and placed in a separate tube. Sterile saline was added at a ratio of 20:1, and the gel-saline mixtures were frozen at −20° C., and thawed again after 6 hours. After three freeze-thaw cycles, the tubes were centrifuged and the supernatants were tested for their procoagulant inducing activity on HUVEC's as described above. In parallel, 12.5% SDS-PAGE's were run using a Phastgel-System (Pharmacia). Active fractions eluted from the SDS-agarose gels were pooled and loaded on ProRPC 15 μm column (Pharmacia), after making them 0.2% trifluoroacetic acid TFA), using a FPLC system (Pharmacia). The column was eluted with a gradient of 0 to 100% B (A: 0.2% TFA in water, B: 0.2% TFA in acetonitrile/isopropanol 1:2). The resulting fractions were lyophilized, and redissolved in tbs containing 0.1% octyl-β-glucoside. For testing their procoagulant activity on HUVEC's, aliquots (50 μl) of the fractions were lyophylized and redissolved in Dulbecco's medium containing 0.5% bovine serum albumin to renature the protein (5). In parallel, aliquots of the fractions were run on 12.5% SDS-PAGE after being lyophylized and redissolved in 5 μl of reducing buffer. Active fractions were pooled, loaded on a Mono Q 5/5 column FPLC (Pharmacia) and eluted with a NaCl gradient. The active fractions again were pooled, diluted in 0.2% TFA/water 1:5 and loaded on a C4-reversed phase column (Vydac), using a HPLC system (Waters LC 625). The elution was performed with a 0 to 100% B gradient (A:0.2% TFA in water, B: 0.2% TFA in acetonitrile/isopropanol 1:2), and fractions were tested described. After this final step, the procoagulant inducing activity was seen to parallel the presence of a single band with Mr corresponding to ≈55,000 Da on nonreduced 12.5% SDS-PAGE. We have termed this material endotoxin-induced thrombosis factor.

Results

Endotoxin-induced thrombosis factor is able to induce procoagulant activity in cultured human endothelial cells. This activity is caused by synthesis and expression of tissue factor on the endothelial cell surface. This can be shown as follows: 1) the activity can be blocked by antihuman-tissue factor-antiserum; 2) the activity can not be demonstrated using human factor VII-deficient plasma; 3) human tissue factor antigen can be assayed using RIA or ELISA; 4) messenger RNA for TF can be assayed using Northern blots. In contrast to endotoxin-induced thrombosis factor, endothelial procoagulant activity is not induced by MIP1, which is purified in a similar way from endotoxin-treated RAW cells (7). In addition, no procoagulant inducing activity was detected in supernatants from RAW cells incubated in medium in the absence of LPS. The procoagulant inducing activity of endotoxin-induced thrombosis factor cannot be blocked by polymyxin, can be destroyed by heating (30 min at 95° C.) and exposure to trypsin (1:100, 37° C., 24 hrs). These data are consistent with the interpretation that the activity of endotoxin-induced thrombosis factor is distinct from endotoxin. A neutralizing rabbit anti-murine TNF-antiserum or a combination of polymyxin and the latter antiserum did not block the activity either (the efficiency of the antiserum was tested using murine TNF), indicating that TNF was not responsible for the observed activity of endotoxin-induced thrombosis factor.

The time course of endotoxin-induced thrombosis factor mediated induction of endothelial tissue factor activity indicated a maximal effect after 6 to 8 hrs, but, in contrast to TNF (3), the effect was still detectable after 60 hrs of incubation (long plateau). The concentration of endotoxin-induced thrombosis factor resulting in half-maximal endothelial tissue factor induction is approximately 150 pM. In terms of a comparison with TNF for the induction of endothelial tissue factor: murine endotoxin-induced thrombosis factor was less effective than human TNF on HUVECs: 1 to 5 nM of endotoxin-induced thrombosis factor had about the same effect as 10 pM TNF. In addition, there is a synergism between endotoxin-induced thrombosis factor and TNF on HUVEC's: 1 nM endotoxin-induced thrombosis factor plus 1 pM TNF has a similar effect to 100 pM TNF. On human monocytes, in contrast, endotoxin-induced thrombosis factor is more effective than TNF for the induction of procoagulant activity; in addition, there is no synergism between endotoxin-induced thrombosis factor and TNF on monocytes. Finally, endotoxin-induced thrombosis factor also induces tissue factor activity in bovine aortic endothelial cells.

Biochemical characterization:

Endotoxin-induced thrombosis factor binds to anion exchange resins over a pH-range between 5 and 10, but not to cation exchange resins. Gel filtration using different resins and buffer systems always resulted in an activity eluting at a molecular weight/size corresponding to 50,000–65,000 Da, based on comparison with standards. On reduced and non-reduced SDS-PAGE, endotoxin-induced thrombosis factor appeared to be a single band with Mr corresponding to $\approx$55,000 Da, indicating a single-chain molecule.

Other biochemical properties of endotoxin-induced thrombosis factor:

Testing additional resins, it could be demonstrated that: endotoxin-induced thrombosis factor binds weakly to hydroxylapatite and lentil lectin columns (the latter indicating the probable presence of sugars on endotoxin-induced thrombosis factor). In contrast, endotoxin-induced thrombosis factor binds tightly to hydrophobic interaction resins, smears off after ethylene glycol (endotoxin-induced thrombosis factor is very hydrophobic). Endotoxin-induced thrombosis factor also binds tightly to reverse phase columns, being eluted more effectively with isopropanol than acetonitrile (there is considerable smearing with the latter solvent).

Endotoxin-induced thrombosis factor can be eluted from SDS-PAGE and agarose-gels with a maximal recovery at 52,000 to 58,000 kD (reduced and non-reduced), but elution of activity is more efficient with agarose gels.

Endotoxin-induced thrombosis factor can be precipitated by ammonium sulfate between 40 and 70% saturation, and by polyethylene glycol at concentrations higher than 15 vol %.

Endotoxin-induced thrombosis factor is not very sensitive to acids for a limited time (30 min), but is denatured by longer treatments (24 hrs). After denaturation by organics and/or acids, endotoxin-induced thrombosis factor activity can be recovered, at least partially, by dilution in PBS or in Dulbecco's Medium with 0.5% bovine serum albumin.

After the reverse phase chromatography step above, the fractions with endotoxin-induced thrombosis factor activity are negative for TNF by Western blotting.

Discussion

These findings demonstrate that endotoxin-induced thrombosis factor has a central role in the host response to Gram negative bacteria. This can be injurious to the host, as it results in alterations in the coagulation mechanism leading to abnormal clotting in the intravascular space. Alternatively, LPS-induced products of macrophages have been shown to induce the necrosis of certain tumors, probably, at least in part, through alterations in tumor blood vessels. Tumor necrosis factor/cachectin, the major identified tumor necrosis factor-inducing agent produced by macrophages so far induces tissue factor in endothelium and macrophages, as does the endotoxin-induced thrombosis factor.

In the setting of septic shock, antibodies and other antagonists of the action of endotoxin-induced thrombosis factor on target cells, especially macrophages and endothelium, could have a protective effect, by preventing the induction of tissue factor and subsequent activation of the coagulation mechanism in the intravascular space. These antibodies could be useful when administered alone, or in the presence of other agents, such as antibodies to tumor necrosis factor (which have been shown to have a partially protective effect when mortality is assessed after the infusion of LPS into mice), inhibitors of LPS, etc. Other types of inhibitors could include peptides derived from endotoxin-induced thrombosis factor or mutant molecules in which amino acid residues have been substituted for the native ones, which bind to the receptor for endotoxin-induced thrombosis factor on target cells, but do not result in activation of effector functions (expression of tissue factor).

Endotoxin-induced thrombosis factor may prove to be effective in inducing the necrosis of certain tumors. It can be administered in the absence of other agents, or in the presence of tumor necrosis factor/cachectin, flavone acetic acid (which can augment the effects of TNF) (unpublished observation) or meth A factor (which also augments the effects of TNF) (8).

These considerations are equally valid for the human counterpart of murine endotoxin-induced thrombosis factor.

REFERENCES

1. Beutler B and Cerami A. Tumor necrosis, cachexia, shock, and inflammation: a common mediator. Ann. Rev. Biochem. 57:505–518, 1988.

2. Remick D, Strieter R, Eskandari M, Nguyen D, Genord M, Raiford C, and Kunkel S. Role of tumor necrosis factor α in lipopolysaccharide-induced pathological alterations. Am. J. Path. 136:49-60, 1990.
3. Nawroth P and Stern D. Modulation of endothelial hemostatic properties by tumor necrosis factor/cachectin. J. Exp. Med. 163:740-745, 1986.
4. Jaffe E. Culture and identification of large vessel endothelial cells, in *Biology of Endothelial Cells*, Jaffe E, editor, Martinus Nijhoff, Boston. pp 1-13.
5. Beutler B. Mahoney J, LeTrang N, Pekala P, and Cerami A. Purification of cachectin, a lipoprotein lipase-suppressing hormone secreted by endotoxin-induced RAW 264.7 cells. J. Exp. Med. 161:984-995, 1985.
6. Laemmli U. Cleavage of structural proteins during the assembly of the head of bacteriophage T4. Nature 227:680-685, 1970.
7. Wolpe S, Davatelis G, Sherry B, Beutler B, Messe D, Nguyen H, Moldawer L, Nathan C, Lowry S, and Cerami A. Macrophages secrete a novel heparin-binding protein with inflammatory and neutrophil chemokinetic properties. J. Exp. Med. 167:570-581, 1988.
8. Clauss M, Murray C, Vianna M, DeWall R, Thurston G, Nawroth P, Gerlach H, Gerlach M, Bach R, Familletti P, and Stern D. A polypeptide factor produced by fibrosarcoma cells that induces endothelial tissue factor and enhances the procoagulant response to tumor necrosis factor/cachectin J. Biol. Chem. in press, 1990.

What is claimed is:

1. A purified endotoxin-induced thrombosis factor comprising a polypeptide characterized by a molecular weight of about 55,000 daltons, by the ability to migrate as a single band on SDS polyacrylamide gels, by the ability to precipitate in ammonium sulfate at saturations from about 40% to 70% and by the ability to precipitate in polyethylene glycol at concentrations above 15%.

2. The purified endotoxin-induced thrombosis factor of claim 1, further characterized by high hydrphobicity, by the ability to bind to a hydroxyapatite column and to a lentil-lectin column, by the ability to bind tightly to a hydrophobic interaction resin and smear off with ethylene glycol, by the ability to bind tightly to a reverse-phase column and elute more effectively with isopropanol than with acetonitrile, by the ability to bind to an anion-exchange resin over a pH range from 5 to 10 and by the inability to bind to a cation-exchange resin.

3. The purified endotoxin-induced thrombosis factor of claim 2, further characterized by resistance to acid denaturation for up to 30 minutes, resistance to polymixin, sensitivity to heating at 95° C. for 30 minutes and sensitivity to trypsin exposure for 24 hours.

4. The purified endotoxin-induced thrombosis factor of claim 3, wherein the thrombosis factor maximally induces tissue factor expression after six to eight hours and continues to induce tissue factor expression for up to sixty hours.

* * * * *